US009827335B2

(12) United States Patent
Bales et al.

(10) Patent No.: US 9,827,335 B2
(45) Date of Patent: *Nov. 28, 2017

(54) TREATING WATER INSOLUBLE NANOPARTICLES WITH HYDROPHILIC ALPHA-HYDROXYPHOSPHONIC ACID CONJUGATES, THE SO MODIFIED NANOPARTICLES AND THEIR USE AS CONTRAST AGENTS

(71) Applicant: General Electric Company, Schenectady, NY (US)

(72) Inventors: Brian Christopher Bales, Niskayuna, NY (US); Bruce Allan Hay, Niskayuna, NY (US); Binil Itty Ipe Kandapallil, Mechanicville, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/919,077

(22) Filed: Oct. 21, 2015

(65) Prior Publication Data
US 2016/0038617 A1 Feb. 11, 2016

Related U.S. Application Data

(63) Continuation of application No. 12/609,799, filed on Oct. 30, 2009, now Pat. No. 9,205,155.

(51) Int. Cl.
*A61K 49/18* (2006.01)
*A61K 49/04* (2006.01)
*B82Y 5/00* (2011.01)

(52) U.S. Cl.
CPC ...... *A61K 49/1857* (2013.01); *A61K 49/0428* (2013.01); *A61K 49/186* (2013.01); *A61K 49/1842* (2013.01); *B82Y 5/00* (2013.01)

(58) Field of Classification Search
None
See application file for complete search history.

(56) References Cited

U.S. PATENT DOCUMENTS

| 5,160,725 | A | 11/1992 | Pilgrimm |
| 5,578,325 | A | 11/1996 | Domb et al. |
| 5,916,539 | A | 6/1999 | Pilgrimm |
| 5,928,958 | A | 7/1999 | Pilgrimm |
| 6,274,121 | B1 | 8/2001 | Pilgrimm |
| 6,541,039 | B1 | 4/2003 | Lesniak et al. |
| 6,638,494 | B1 | 10/2003 | Pilgrimm |
| 7,208,135 | B2 | 4/2007 | Sterzel |
| 2003/0157179 | A1 | 8/2003 | Blum et al. |
| 2003/0229280 | A1 | 12/2003 | Greb et al. |
| 2004/0023030 | A1 | 2/2004 | Bonitatebus, Jr. et al. |
| 2004/0105980 | A1 | 6/2004 | Sudarshan et al. |
| 2004/0161435 | A1 | 8/2004 | Gupta |
| 2004/0253181 | A1 | 12/2004 | Port et al. |
| 2006/0024235 | A1 | 2/2006 | Pilgrimm |
| 2006/0093555 | A1 | 5/2006 | Torres et al. |
| 2006/0204238 | A1 | 9/2006 | Cho et al. |
| 2007/0129465 | A1 | 6/2007 | Baran, Jr. |
| 2007/0281034 | A1 | 12/2007 | Kirpotin et al. |
| 2008/0156736 | A1 | 7/2008 | Hirai et al. |
| 2008/0299046 | A1 | 12/2008 | White et al. |
| 2009/0028792 | A1 | 1/2009 | Schwartz et al. |
| 2009/0054555 | A1 | 2/2009 | Baldi et al. |
| 2009/0092554 | A1 | 4/2009 | Skaff et al. |
| 2009/0111919 | A1 | 4/2009 | Lortz et al. |
| 2010/0086927 | A1 | 4/2010 | Menchen et al. |
| 2010/0166664 | A1 | 7/2010 | Butts et al. |
| 2010/0215586 | A1 | 8/2010 | Port et al. |

FOREIGN PATENT DOCUMENTS

| CN | 1654551 A | 8/2005 |
| DE | 3343586 A1 | 6/1985 |
| DE | 3440190 A1 | 5/1986 |
| DE | 3443810 A1 | 5/1986 |
| DE | 3624626 A1 | 1/1988 |
| DE | 3709852 A1 | 10/1988 |
| DE | 4309333 A1 | 9/1994 |

(Continued)

OTHER PUBLICATIONS

Daou, T.J. et al., "Phosphate Adsorption Properties of Magnetite-Based Nanoparticles", Chem. Mater., vol. 19, pp. 4494-4505 (2007).

Daou, T.J. et al., "Water soluble dendronized iron oxide nanoparticles", Dalton Transactions, pp. 4442-4449 (Apr. 2009).

Goff, J.D. et al., "Novel Phosphonate-Functional Poly(ethylene oxide)-Magnetite Nanoparticles Form Stable Colloidal Dispersions in Phosphate-Buffered Saline", Chem. Mater., vol. 21, pp. 4784-4795 (2009).

Joumaa, Nancy et al., "Surface Modification of Iron Oxide Nanoparticles by a Phosphate-Based Macromonomer and Further Encapsulation into Submicrometer Polystyrene Particles by Miniemulsion Polymerization", Journal of Polymer Science: Part A: Polymer Chemistry, vol. 46, pp. 327-340 (2008).

(Continued)

*Primary Examiner* — Jake Vu
(74) *Attorney, Agent, or Firm* — Pabitra K. Chakrabarti

(57) ABSTRACT

The present application discloses treating water insoluble nanoparticles, particularly nanoparticles of metals and metal compounds which find utility in diagnostic imaging such as MR and X-ray imaging, with an alpha-hydroxyphosphonic acid conjugate with a hydrophilic moiety to render the nanoparticles sufficiently hydrophilic to find utility in diagnostic imaging. Among the modified hydrophilic nanoparticles disclosed are those in which the hydrophilic moieties of the modifying conjugate are ethylene oxide based polymers and copolymers and zwitterions and the nanoparticles are composed of transition metal oxides such as superparamagnetic iron oxide and tantalum oxide. Disclosed are nanoparticles which are sufficiently hydrophilic to form stable aqueous colloidal suspensions. Also disclosed is diagnostic imaging such as MR and X-ray using the modified hydrophilic nanoparticles as contrast agents.

15 Claims, 3 Drawing Sheets

(56) References Cited

FOREIGN PATENT DOCUMENTS

| EP | 0137926 | A1 | 4/1985 |
|---|---|---|---|
| JP | 5651493 | A | 5/1981 |
| WO | 03016217 | A1 | 2/2003 |
| WO | 2006124670 | A2 | 11/2006 |
| WO | 2007065935 | A1 | 6/2007 |
| WO | 2008017721 | A2 | 2/2008 |
| WO | 2009015056 | A1 | 1/2009 |
| WO | 2009029053 | A1 | 3/2009 |
| WO | 2009051392 | A2 | 4/2009 |
| WO | 2009053596 | A2 | 4/2009 |
| WO | 2009076673 | A2 | 6/2009 |
| WO | 2009109588 | A2 | 9/2009 |

OTHER PUBLICATIONS

Lalatonne, Y. et al., "Bis-phosphonates—ultra small superparamagnetic iron oxide nanoparticles: a platform towards diagnosis and therapy", Chem. Commun., pp. 2553-2555 (2008).

Laurent, S. et al, "Magnetic Iron Oxide Nanoparticles: Synthesis, Stabilization, Vectorization, Physicochemical Characterizations, and Biological Applications", Chem. Rev., vol. 108, pp. 2064-2110 (2008).

Liu, L.-H. et al., "Photoinitiated Coupling of Unmodified Monosaccharides to Iron Oxide Nanoparticles for Sensing Proteins and Bacteria", Bioconjugate Chem., vol. 20, pp. 1349-1355 (Jun. 2009).

Mohapatra, S. et al., "Synthesis and stability of functionalized iron oxide nanoparticles using organophosphorus coupling agents", Colloids and Surfaces A: Physicochem. Eng. Aspects, vol. 339, pp. 35-42 (Jan. 2009).

Na, H.B. et al., "Versatile PEG-derivatized phosphine oxide ligands for waterdispersible metal oxide nanocrystals", Chem. Commun., pp. 5167-5169 (2007).

Portet, D. et al., "Comparative Biodistribution of Thin-Coated Iron Oxide Nanoparticles TCION: Effect of Different Bisphosphonate Coatings", Drug Development Research, vol. 54, pp. 173-181 (2001).

Sahoo, Y. et al., "Alkyl Phosphonate/Phosphate Coating on Magnetite Nanoparticles: A Comparison with Fatty Acids", Langmuir, vol. 17, pp. 7907-7911 (2001).

Traina, C.A. et al., "Surface Modification of Y2O3 Nanoparticles", Langmuir, vol. 23, pp. 9158-9161 (2007).

Tromsdorf, U.I. et al., "A Highly Effective, Nontoxic T1 MR Contrast Agent Based on Ultrasmall PEGylated Iron Oxide Nanoparticles", Nano Letters, Downloaded on Oct. 5, 2009 | http://pubs.acs.org Publication Date (Web): Oct. 2, 2009 | doi: 10.1021/nl902715v.

Fu, Lei et al., "Self-assembled (SA) bilayer molecular coating on magnetic nanoparticles", Applied Surface Science, vol. 181, pp. 173-178 (2001).

International Search Report from corresponding PCT Application No. PCT/EP2010/066429 dated Jun. 8, 2011.

Portet et al., "Nonpolymeric Coatings of Iron Oxide Colloids for Biological Use as Magnetic Resonance Imaging Contrast Agents", Journal of Colloid and Interface Science, vol. No. 238, No. 1, pp. 37-42, Jul. 1, 2001.

Podstawka et al., "Adsorption mechanism of physiologically active 1-phenylalanine phosphonodipeptide analogues: Comparison of colloidal silver and macroscopic silver substrates", Surface Science, vol. No. 601, No. 21, pp. 4971-4983, Oct. 26, 2007.

Zhang et al., "Facile controlled preparation of phosphonic acid-functionalized gold nanoparticles", Journal of Colloid and Interface Science 2010 Academic Press Inc., vol. No. 351, No. 2, pp. 421-426, Nov. 2010.

Yao et al., "Soluble Precipitable Porphyrins for Use in Targeted Molecular Brachytherapy", New J. Chem., vol. No. 32, pp. 436-451, 2008.

Japanese Office Action issued in connection with corresponding JP Application No. 2012-535840 dated Sep. 8, 2015.

Unofficial English Translation of Japanese Notice of Allowance issued in connection with corresponding JP Application No. 2012-535840 dated Aug. 2, 2016.

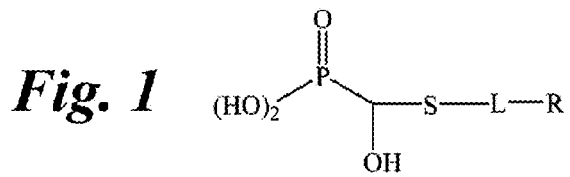

Fig. 1

S is a single bond or an aliphatic, cycloaliphatic or aromatic group of between 1 and 10 carbon atoms, L is a single bond or a linkage selected from the group consisting of ester, ether, secondary or tertiary amine, quaternary group, urea, carbamate and amide and R is a hydrophilic moiety.

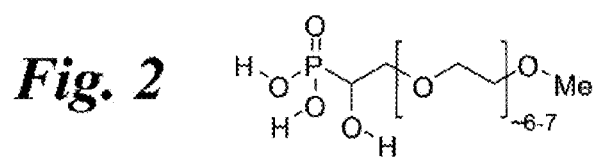

Fig. 2

PEG-350 monomethyl ether alpha-hydroxy phosphonic acid

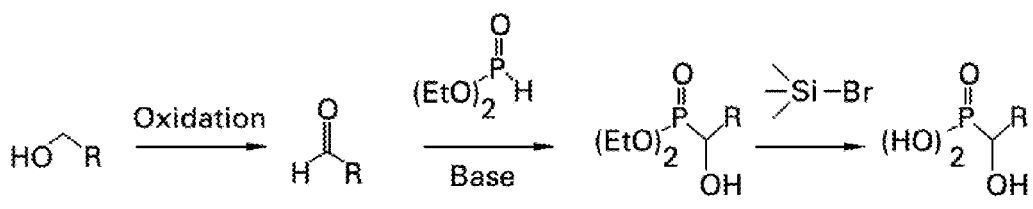

A synthetic scheme for α-hydroxy phosphonic acids

Fig. 3

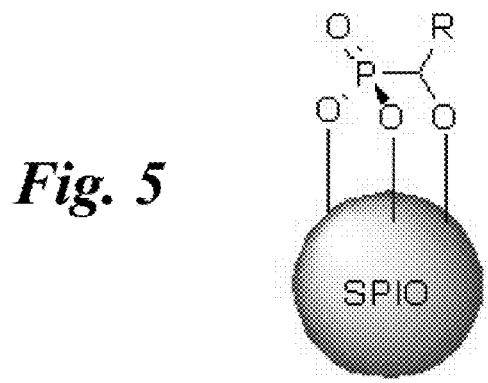

Fig. 5

Synthesis of α-Hydroxy PEG-350 Phosphonic Acid

TREATING WATER INSOLUBLE NANOPARTICLES WITH HYDROPHILIC ALPHA-HYDROXYPHOSPHONIC ACID CONJUGATES, THE SO MODIFIED NANOPARTICLES AND THEIR USE AS CONTRAST AGENTS

CROSS REFERENCE TO RELATED APPLICATIONS

This application is a continuation of U.S. patent application Ser. No. 12/609,799, filed on Oct. 30, 2009.

BACKGROUND

The invention relates generally to treating nanoparticles, particularly those based on transition metal oxides, to render them sufficiently hydrophilic to form stable aqueous suspensions and therefore be useful in applications requiring hydrophilicity such as contrast agents in diagnostic imaging such as MRI and X-ray, to the hydrophilic nanoparticles resulting from said treatment, to said stable aqueous suspensions and to the use of said hydrophilic nanoparticles as contrast agents in said imaging. Nanoparticles, i.e. particles whose diameters are appropriately measured in nanometers, have been considered for a wide variety of end uses. Some of these uses require some degree of hydrophilicity but the material upon which some nanoparticles are based may lack this attribute. For instance, nanoparticles with appropriate imaging properties for use as contrast agents for MR and X-ray imaging are typically based on transition metal oxides which lack suitable hydrophilicity. Therefore efforts have been made to modify the surface properties of these nanoparticles to be more compatible with aqueous media and give these nanoparticles the ability to form stable aqueous suspensions. However, in some applications such as use as contrast agents it is also desirable that the nanoparticles have a monodisperse particle size distribution and any surface treatment that results in a polydisperse particle size distribution such as non-uniform aggregation by complexation in a biological matrix based on carbohydrates with carboxylate groups is problematic. In addition, in some applications such as in vivo use as contrast agents it is desirable that the surface treatment have a well defined reproducible structure and be amenable to safety testing. Silane based surface treatments can be problematic because they can undergo self condensation that interferes with these goals.

In addition, there has been a need for hydrophilic nanoparticles that do not suffer a degradation of their hydrophilicity as a result of purification and display suspension stability in aqueous mediums containing electrolytes. For instance, in the preparation of contrast agents for in vivo use in human subjects the candidate nanoparticles would typically be subjected to filtration and be expected to show suspension stability in isotonic aqueous media, i.e. media containing about 150 mM NaCl. There have been efforts to use the adhesion of phosphates for transition metal oxides to impart this type of hydrophilicity to nanoparticles using phosphate based materials alone, such as polyphosphoric acid, or linked to hydrophilic moieties, such as polyethylene glycol. In this regard, there is a preference for hydrophilic moieties with an essentially neutral zeta potential for in vivo use in human subjects to avoid undesirable interactions with human tissue. However, such efforts have not yielded so hydrophilically modified nanoparticles that display the desired stability as a colloidal suspension in a 150 mM NaCl aqueous medium after filtration. For instance, such efforts have not yielded suspensions which display an essentially stable (no increase in hydrodynamic diameter ($D_H$)) particle size as measured by dynamic light scattering (DLS) after tangential flow filtration with a 30 kDa cut off and storage for more than a week in such an aqueous medium.

BRIEF DESCRIPTION

The present invention involves the discovery of the superior performance of conjugates of α-hydroxyphosphonic acid and a hydrophilic moiety which are linked via, the carbon atom carrying the α-hydroxy group as agents to improve the hydrophilicity of water insoluble nanoparticles, particularly nanoparticles based on transition metal oxides. The conjugate linkage preserves all three of the α-hydroxyphosphonic acid's hydroxyl groups and this is believed to give the conjugate superior adhesion to nanoparticles. In some embodiments the conjugate has the following Structure 1:

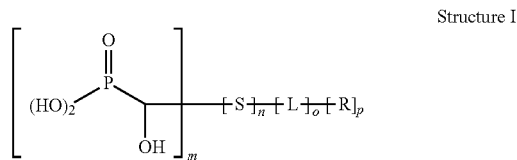

Structure I wherein S is a spacer, L is a linkage between S and R and R is a hydrophilic moiety and m and p are 1-5 and n and o are 0-5. In some embodiments, S is a direct bond, an unsubstituted or substituted aliphatic or cycloaliphatic group, an unsubstituted or substituted aryl group, a heteroaliphatic group or a heteroaryl group and in some cases is a straight chain alkyl group of 1 to 10 carbon atoms in length and L is a direct bond, carbonyl group, ether group, ester group, secondary or tertiary amine, quaternary amine group, amide group, carbamate group or urea group. Suitable nanoparticles are those which are not soluble in water in the classic sense in which the the individual molecules of the solute are uniformly dispersed in the solvent in the manner of sugar or table salt in water. Thus the treatment of nanoparticles which possess some degree of suspensability in water with the alpha-hydroxyphosponic acid conjugates and the resultant nanoparticles with the conjugates adhered are included in the present invention.

It is of particular interest that the conjugate not include groups or moieties which could have undesirable reactions with human tissue. Thus, it is convenient that the conjugate display a zeta potential between about −40 mV and 40 mV, preferably between about −15 mV and 15 mV when adhered to a nanoparticle with it being especially interesting that it display an essentially neutral zeta potential when so adhered. This is conveniently accomplished by utilizing zwitterions or non-ionic moieties as the hydrophilic moiety.

The hydrophilic moieties may be monomeric or polymeric but it is convenient that they have an essentially neutral net ionic charge. Among the polymeric hydrophilic moieties those polyethers at least partially based on ethylene oxide units such as ethylene oxide/propylene oxide copolymers and polyethylene glycol are of especial interest. Monomeric hydrophilic moieties with no net charge, particularly zwitterions, are convenient for conjugates used to treat nanoparticles to be used in vivo with human subjects because of the greater ease in characterizing them for safety evaluations. Among these those based on 4-piperadinecarboxylic acid are of especial interest.

It is also convenient for conjugates used to treat nano articles to be used in vivo with human subjects that the linkage between the α-hydroxyphosphonic acid and a hydrophilic moiety be a hydrocarbon, i.e., in Structure I, S is a single bond. This minimizes the probability of any interaction between such treated nano articles and human tissue. In this regard, conjugates of the following Structures II and III are of particular interest:

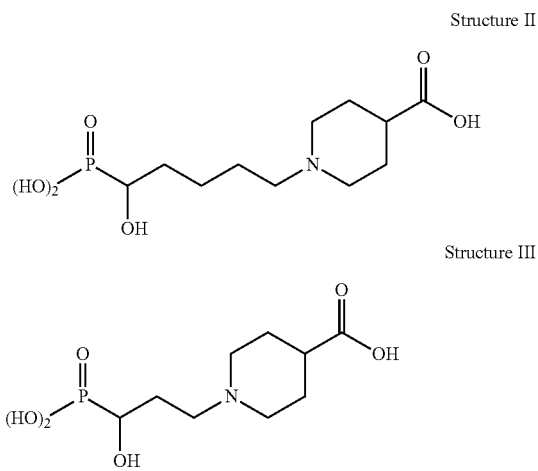

The conjugate is preferably sufficiently hydrophilic that when it is used to treat nanoparticles at a ratio of about two conjugates per nanoparticle it will render the nanoparticles capable of forming stable colloidal suspensions in aqueous media with a $D_H$ determined by DLS of about 500 nm or less. It is particularly convenient that it render so treated nanoparticles hydrophilic enough to display a value of less than one for the log of the distribution coefficient between equal volumes of n-octanol and 0.1 M pH 7.0 3-(N-morpholino) propanesulfonic acid (MOPS) buffer.

The nanoparticles that are treated with the conjugate to achieve greater hydrophilicity are preferably based upon transition metals and transition metal compounds such as oxides, carbides, sulfides, nitrides, phosphides, borides, halides, selenides, tellurides and combinations thereof. Oxides are of particular interest. It is believed that the oxide structure contributes to the adhesion of the α-hydroxyphosphonic acid. Transition metal compounds are useful for preparing contrast agents for MR and X-ray imaging. The transition metals of the third period of the Periodic Table of Elements are useful for forming compounds that display paramagnetism and conveniently superparamagnetism and therefore are useful as MRI contrast agents. Especially convenient are superparamagnetic nanoparticles based upon iron oxide and optionally cobalt, copper, manganese, nickel or combinations thereof. Of these, the most convenient are nanoparticles based upon magnetite, maghemite or combinations that are about 15 nm or less in diameter and display superparamagnetism. These are commonly referred to as superparamagnetic iron oxide (SPIO) particles. Transition metals with atomic numbers greater than 34 and zinc are useful for preparing compounds useful as X-ray contrast agents. Among these hafnium, molybdenum, silver, tantalum, tungsten, and zirconium are of particular interest with tantalum and particularly tantalum oxide being the most convenient.

The hydrophilically modified nanoparticles typically have a $D_H$ as determined by DLS of 500 nm or less. It is convenient that their $D_H$ be 50 nm or less, more preferably 30 nm or less and most preferably that $D_H$ be between 3 and 30 nm. If the hydrophilically modified nanoparticles are destined for in vivo use in human subjects as, for instance, MRI or X-ray contrast agents, a particularly convenient $D_H$ is about 8 nm or less.

The hydrophilically modified nanoparticles are conveniently prepared by reacting them with the conjugate. A convenient approach is to form a colloidal suspension of the nanoparticles in an organic solvent such as tetrahydrofuran (THF) and then mix it with an organic solution of the conjugate in the same or a different organic solution. The mixture may then be held for an elevated temperature for an extended period until the reaction is essentially complete. Typically temperatures of 50° C. or more for 16 hours or more are convenient.

Stable monodisperse aqueous colloidal suspensions of the hydrophilically modified nanoparticles are readily obtained. Such suspensions should preferably be stable against filtration such as tangential flow filtration against a 30 kDa cut off and the addition of electrolytes such as the addition of NaCl to render the aqueous medium isotonic, i.e. about 150 mM of NaCl. Preferably the suspensions are stable for storage periods of one week or greater and more preferably are stable against not only sedimentation but also against growth of the $D_H$ as determined by DLS of the suspended nanoparticles. If the suspensions are intended for in vivo use in human subjects it is convenient to render them isotonic by the addition of NaCl, dextrose or combinations thereof.

The stable monodisperse aqueous colloidal suspensions are conveniently prepared by diluting a colloidal suspension in an organic solvent. A convenient approach is to simply dilute the organic solvent or solvents in which the nanoparticles have been reacted with the conjugate by the addition of water. Another approach is to react a colloidal suspension of the nanoparticles in an organic solvent with the conjugate in water. In either case it is convenient to remove the unreacted reactants by filtration or organic extraction with a solvent such as hexane or a combination. Any volatiles in the aqueous phase after solvent extraction can be removed by the application of a partial vacuum. Then the hydrophilically modified nanoparticles can be purified by tangential flow filtration against a 30 kDa filter.

The hydrophilically modified nanoparticles may be conveniently used as contrast agents in diagnostic imaging. Common types of such diagnostic imaging are MR and X-ray imaging. In either case, it is convenient to use hydrophilically modified nanoparticles which have a zeta potential between about −15 mV and 15 mV. A convenient approach in the in vivo imaging of human subjects is to administer the nanoparticles intraveneously, preferably as a stable isotonic aqueous suspension. If the imaging is to be by MR the nanoparticles should comprise a paramagnetic, preferably superparamagnetic species, and most preferably they should be iron oxide based such as magnetite or maghemite. If the imaging is to be by X-ray the nanoparticles should comprise a transition metal compound of a metal with an atomic number greater than 34 or zinc, preferably gold, hafnium, molybdenum, silver, tantalum, tungsten or zirconium and most preferably they should be tantalum oxide based. In a particularly interesting embodiment, the hydrophilically modified nanoparticles have a $D_H$ of 8 nm or less and clear the body of the subject via the kidney.

DRAWINGS

These and other features, aspects, and advantages of the present invention will become better understood when the following detailed description is read with reference to the accompanying drawings in which like characters represent like parts throughout the drawings, wherein:

FIG. 1 is a generic structural formula for suitable alpha-hydroxy phosphonic acids with which to make hydrophilic nanoparticles.

FIG. 2 is the structural formula for a particularly interesting alpha-hydroxy phosphonic acid with which to make hydrophilic nanoparticles wherein Me is a methyl group.

FIG. 3 is a synthetic route to alpha-hydroxy phosphonic acids with attached hydrophilic moieties R.

FIG. 5 is a hypothetical schematic representation of the attachment of an alpha-hydroxy phosphonic acid of the type whose synthesis is illustrated in FIG. 3 with a hydrophilic moiety R attached to a superparamagnetic iron oxide SPIO nanoparticle.

DETAILED DESCRIPTION

Figure 4:
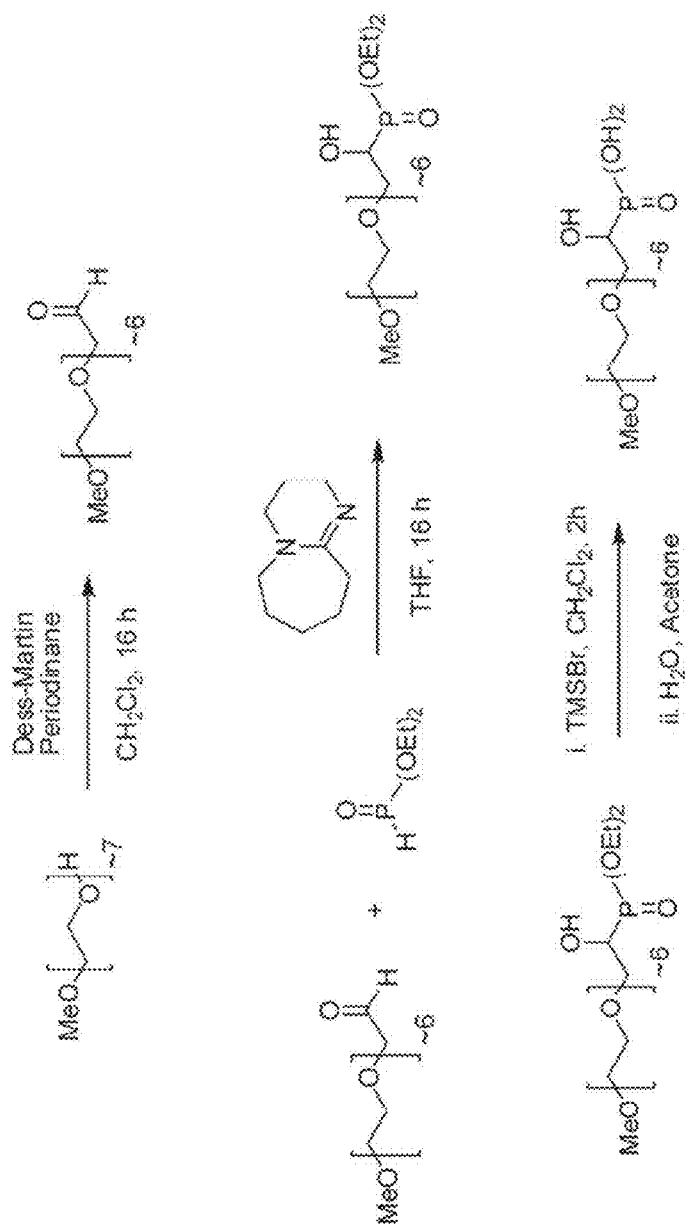
FIG. 4 is a synthetic route to the particularly interesting alpha-hydroxy phosphonic acid shown in FIG. 2.
Figure 6C:
FIG. 6C is a difference map of the differences between FIG. 6A and FIG. 6B.
Figure 6F:
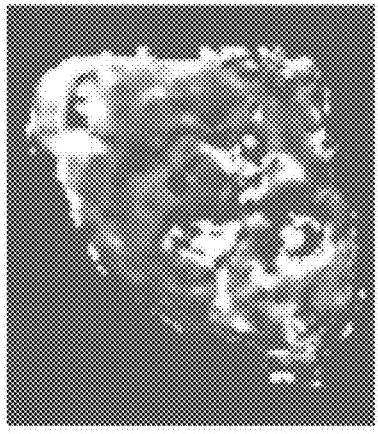
FIG. 6F is an $R_2^*$ relaxation difference map of the differences between FIG. 6D and FIG. 6E exhibiting a clear distinction between tumor and muscle tissue.
Figure 6B:
FIG. 6B is a $T_1$ weighted image (TE=4.1 ms) of a tumor in accordance Example 12, 30 minutes after the administration of the nanoparticle contrast agent of Example 4.
Figure 6E:
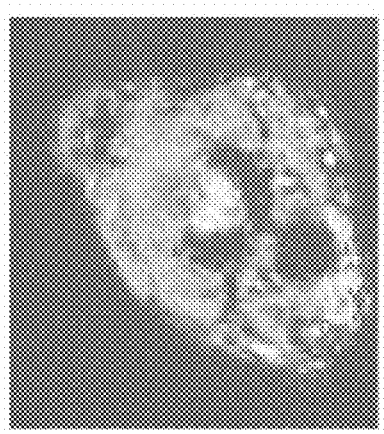
FIG. 6E is a $T_2^*$-weighted image (TE=18.4 ms) of a tumor in accordance Example 12 30 minutes after the administration of the nanoparticle contrast agent of Example 4.
Figure 6A:
FIG. 6A is a $T_1$ weighted image (TE=4.1 ms) of a tumor in accordance Example 12 without contrast agent.
Figure 6D:
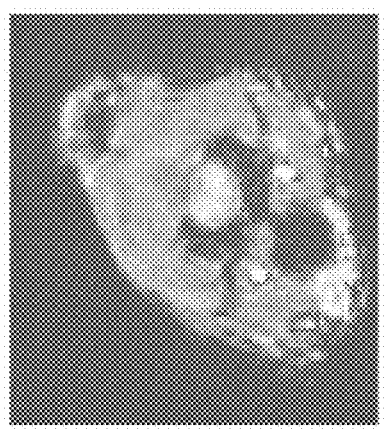
FIG. 6D is a $T_2^*$-weighted image (TE=18.4 ms) of a tumor in accordance Example 12 without contrast agent.

The conjugates of the present invention are broadly defined to have a wide variety of linkages and hydrophilic moieties. The key feature is that the conjugate has the three hydroxyl groups of the α-hydroxy phosponic acid that are chemically and sterically accessible. While the structure has chiral centers it is expected that all of the individual enantiomers and possible racemic mixtures would be suitable to impart hydrophilicity to water insoluble nanoparticles.

These conjugates may have any of the commonly known chemical linkages between the α-hydroxy phosponic acid structure and the hydrophilic moiety including those based upon carbon, nitrogen, oxygen and sulfur. Groups of particular interest are hydrocarbon, carbonyl, ester, ether, secondary or tertiary amine, quaternary amine, urea, carbamate and amide. The intended end use of the nanoparticles to be treated with the conjugate may impact the choice of linkage group. For instance if the nanoparticles are to be used in vivo, particularly in human subjects, it may be desirable to avoid linkages such as quaternary groups which might result in interactions with tissue components such as proteins. The most interesting linkage group from the standpoints of inertness is a hydrocarbon.

The hydrophilic moiety can be any of those moieties known to have good compatibility with water including those known as surfactants. They can be anionic, cationic or non-ionic. The hydrophilic moiety may be a carbohydrate such as mono, di or oligosaccharide, a non-carbohydrate monomeric polyalcohol, a polyether with ethylene oxide groups, a non-carbohydrate polymer, other than a polyethers with ethylene oxide groups, which has pendant hydroxyl groups such as polyvinyl alcohol, poly(ethylene imine), an aliphatic or cycloaliphatic amine and combinations thereof.

In some embodiments, the hydrophilic moieties are based on ethylene oxide with the poly(ethylene oxides) being of specific interest, particularly those with molecular weights equal to or less than about 5000 daltons, especially those with molecular weights equal to or less than about 2000 daltons. The poly(ethylene oxides) with molecular weights of about 350 daltons are of particular interest.

The hydrophilic moiety can also be a zwitterion having one or more positively charged moieties, one or more negatively charged moieties and a spacer group in between the charged moieties. For the purposes of this application, combinations of positively charged moieties and negatively charged moieties are considered zwitterions if at physiological pH values they display essentially no net charge. Suitable positively charged moieties include protonated primary amines, protonated secondary amines, protonated tertiary alkyl amines, quanternary alkyl amines, protonated amidines, protonated guanidines, protonated pyridines, protonated pyrimidines, protonated pyrazines, protonated purines, protonated imidazoles, protonated pyrroles or combinations thereof, suitable negatively charged moieties include deprotonated carboxylic acids, deprotonated sulfonic acids, deprotonated sulfinic acids, deprotonated phosphonic acids, deprotonated phosphoric acids, deprotonated phosphinic acids, or combinations thereof and suitable spacer groups include unsubstituted and substituted aliphatic, cycloaliphatic and aryl groups, heteroaliphatic groups, heteroaryl groups, ethers, amides, esters, carbamates, ureas, or combinations thereof. In one embodiment, spacer groups include straight chain alkyl groups of 1 to 10 carbon atoms in length.

If the intended end use of the nanoparticles is compatible with the modified hydrophilic nanoparticles with the adhered alpha-hydroxyphosponic acid conjugates having a net ionic charge, the hydrophilic moiety may be any of the positively charged moieties or any of the negatively charged moieties discussed above as suitable for the formation of zwitterions.

The intended end use of the nanoparticles to be treated with the conjugate may impact the choice of hydrophilic moiety. For instance if the nanoparticles are to be used in vivo, particularly in human subjects, it may be desirable to avoid hydrophilic moieties such as ionic groups which might result in interactions with tissue components such as proteins. For in vivo use, hydrophilic moieties with essentially no net charge such as zwitterions and polyethers with ethylene oxide units are of particular interest. For use with human subjects, hydrophilic moieties that are easily and reproducibly characterized for safety evaluation such as monomeric moieties are particularly convenient. Particularly convenient hydrophilic moieties are those based on 4-piperadinecarboxylic acid which are both monomeric and as zwitterions carry no net charge. For applications in which toxicity is less of a concern such as the in vitro inoculation of cell cultures poly(ethylene)imines may be appropriate hydrophilic moieties.

Particularly suitable zwitterions are disclosed in U.S. patent application Ser. No. 12/344,604 filed 29 Dec. 2008, incorporated by reference herein. These include hydrophilic moieties which contain cationic nitrogens and anionic carboxylic, phosphoric and sulfonic acid based groups such as N,N-dimethyl-3-sulfo-N-(3-propyl)propan-1-aminium, 3-(methyl)propyl)amino)propane-1-sulfonic acid, 3-(propylamino)propane-1-sulfonic acid, 2-(ethoxy(hydroxy)phosphoryloxy)-N,N,N-trimethylethanaminium, 2ethyl(hydroxy)phosphoryloxy)-N,N,N-trimethylethanaminium, N,N,N-trimethyl-3-(N-propionylsulfamoyl) propan-1-aminium, N-((2H-tetrazol-5-yl)methyl)-N,N-dimethyl-propan-1-aminium, N-(2-carboxyethyl)-N,N-dimethyl-propan-1-aminium, 3-(methylpropyl)amino)propanoic acid, 3-(propylamino) propanoic acid, N-(carboxymethyl)-N,N-dimethyl-propan-1-aminium, 2-(methylamino)acetic acid, 2-(propylamino)acetic acid, 2-(4-propylcarbamoyl) piperazin-1-yl) acetic acid, 3-(4propylcarbamoyl) piperazin-1-yl) propanoic acid, 2-(methyl(2-propylureido)ethyl)amino)acetic acid and 2-(2-(propylureido)ethyl)amino acetic acid.

Suitable hydrophilic polyether based hydrophilic moieties are disclosed in U.S. Pat. No. 5,916,539 issued 29 Jun. 1999, which is incorporated herein by reference. These include polyethylene glycols (PEG's) of various molecular weights with various terminal groups including amino and hydroxyl as well as copolymers with polypropylene glycol (PPG).

The conjugate is preferably sufficiently hydrophilic that it can render nanoparticles able to form stable aqueous suspensions when it is reacted with the nanoparticles at a ratio of two moles of conjugate to one mole of the metal basis of the nanoparticle. In this regard, the nanoparticle will typically be based on a transition metal compound such as an oxide or a transition metal itself. It is convenient to specify the reaction ratio using the moles of elemental metal as this can be readily obtained from an elemental analysis of the starting suspension of nanoparticles in organic solvent. From a knowledge of the chemical make up of the nanoparticles and their average size before treatment, a rough calculation can be made of the amount of conjugate per nanoparticle. It is particularly convenient that the conjugate be hydrophilic enough to give nanoparticles of iron oxide or tantalum oxide of less than 15 nm treated at this ratio sufficient hydrophilicity to display a value of less than one for the log of the distribution coefficient between equal volumes of n-octanol and 0.1 M pH 7.0 MOPS buffer.

It is of particular interest that the modified hydrophilic nanoparticles with an adhered alpha-hydroxyphosphonic acid conjugate be sufficiently hydrophilic to form a stable aqueous colloidal suspension that exhibits no substantial change in hydrodynamic diameter $(D_H)$ as determined by dynamic light scattering (DLS) in 150 mM NaCl water after tangential flow filtration and storage for one week at room temperature.

The nanoparticles that are to be treated with the conjugate can be of any water insoluble material that can be formed into particles of 500 nm or less to which the α-hydroxy phosphonic acid portion of the conjugate will adhere. It is of interest to use nanoparticles that have utility as contrast agents in MR or X-ray imaging. However, nanoparticles for other end uses such as infusion of cell cultures for transfection of genes are also of interest.

For use as MRI contrast agents the basis of the nanoparticles should be a metal or its compounds that are paramagnetic, with those that are superparamagnetic being of particular interest. These metals are conveniently drawn from the transition metals of Period III of the Periodic Table of Elements beginning with manganese and ending with zinc. A particularly interesting group of materials are those based upon iron oxide. Especially convenient materials are those known as SPIO's. These materials have the general formula $[Fe_2^+O_3]_x[Fe_2^+O_3(M^{2+}O)]_{1-x}$ where $1 \geq x \geq 0$. $M^{2+}$ may be a divalent metal ion such as iron, manganese, nickel, cobalt, magnesium, copper, zinc or a combination thereof. When the metal ion $(M^{2+})$ is ferrous ion $(Fe^{2+})$ and x=0, the material is magnetite $(Fe_3O_4)$, and when x=1, the material is maghemite $(\gamma\text{-}Fe_2O_3)$.

In general, superparamagnetism occurs when crystal-containing regions of unpaired spins are sufficiently large that they can be regarded as thermodynamically independent, single domain particles called magnetic domains. These magnetic domains display a net magnetic dipole that is larger than the sum of its individual unpaired electrons. In the absence of an applied magnetic field, all the magnetic domains are randomly oriented with no net magnetization. Application of an external magnetic field causes the dipole moments of all magnetic domains to reorient resulting in a net magnetic moment. In some embodiments, these materials demonstrate a spinel crystalline structure as shown by transmission electron microscope (TEM) analysis.

For use as X-ray contrast agents, the basis of the nanoparticles should be a metal or its compounds that are substantially more radiopaque than materials typically found in living organisms. It is convenient to use materials with an effective atomic number greater than or equal to 34 when at a concentration of approximately 50 mM. Such materials are likely yield appropriate contrast enhancement of about 30 Hounsfield units (HU) or greater, which is a minimum enhancement of particular interest. Examples of transition metal elements that may provide this property include tungsten, tantalum, hafnium, zirconium, molybdenum, silver, and zinc. Tantalum oxide is one particular example of a suitable core composition for use in X-ray imaging applications. Of especial interest are materials that lead to a CT signal in a range from about 100 Hounsfield to about 5000 Hounsfield units.

The modified hydrophilic nanoparticles to which the alpha-hydroxyphosphonic acids have been adhered may be used as contrast agents in diagnostic imaging. In such an application, these nanoparticles are administered to a subject, in some embodiments a mammalian subject, and then the subject is subjected to imaging. These nanoparticles have particular utility in MR and X-ray imaging though they may also find utility as contrast agents in ultrasound or radioactive tracer imaging.

When used in diagnostic imaging, particularly of mammalian subjects and more particularly of human subjects, the modified hydrophilic nanoparticles to which the alpha-hydroxyphosphonic acids have been adhered are typically taken up in a pharmaceutically acceptable carrier which may or may not comprise one or more excipients. If the administration is to be by injection, particularly parenteral injection, the carrier is typically an aqueous medium that has been rendered isotonic by the addition of about 150 mM of NaCl, 5% dextrose or combinations thereof. It typically also has the physiological pH of between about 7.3 and 7.4. The administration may be intravascular (IM), subcutaneous (SQ) or most commonly intravenous (IV). However, the administration may also be via implantation of a depot that then slowly releases the nanoparticles to the subject's blood or tissue.

Alternatively, the administration may be by ingestion for imaging of the GI tract or by inhalation for imaging of the lungs and airways.

The administration to human subjects, particularly IV administration, requires that the modified hydrophilic nanoparticles to which the alpha-hydroxyphosphonic acids have been adhered be non-toxic in the amounts used and free of any infective agents such as bacteria and viruses and also free of any pyrogens. Thus, these nanoparticles should be stable to the necessary purification procedures and not suffer a degradation in their hydrophilicity.

These nanoparticles may be delivered to the site of administration as a stable aqueous colloidal suspension with the proper osmolality and pH, as a concentrated aqueous colloidal suspension suitable for dilution and adjustment or as a powder, such as obtained by lyophilization, suitable for reconstitution.

Example 1

Synthesis of a PEG-350 Conjugate

Synthesis of PEG-350 Mono(Methyl Ether) Acetaldehyde

To a solution containing PEG-350 mono(methyl ether) (3.438 g, 9.82 mmol) dissolved in $CH_2Cl_2$ (98 mL) was added Dess-Martin Periodinane (5.00 g, 11.79 mmol) and the resulting solution was stirred at rt for 20 h. During the reaction a fine, white precipitate was formed and was removed at the end of the reaction via filtration through a celite pad. The solvent was removed from the filtrate in vacuo to leave a white solid suspended in a yellow oil. The solid was triturated with diethyl ether, and the solid was removed by filtration through a celite pad. Removal of the solvent from the filtrate in vacuo left the product PEG-350 mono(methyl ether) acetaldehyde (3.42 g, 100%) as a yellow oil. $^1$H NMR ($CDCl_3$) δ 9.73 (t, J=4 Hz, 1H), 4.16 (d, J=4 Hz, 2H), 3.65 (m, 24H), 3.38 (s, 3H) ppm. IR (neat) 2873, 1732, 1455, 1350, 1109, 1040, 948, 851, 749 $cm^{-1}$.

Synthesis of Diethyl α-Hydroxy PEG-350 Mono(Methyl Ether) Phosphonate

To a solution containing PEG-350 mono(methyl ether) acetaldehyde (3.71 g, 10.7 mmol) dissolved in tetrahydrofuran (53 mL) was added diethyl phosphite (1.77 g, 12.8 mmol). The solution was cooled to 0° C., and 1,8-diazabicyclo[5.4.0]undec-7-ene (1.94 g, 12.8 mmol). After stirring at 0° C. for 10 min, the rxn was warmed to rt and stirred for an additional 24 h. The solvent was removed in vacuo to leave a dark yellow oil which was purified via column chromatography (100% $CH_2Cl_2$ to 15% MeOH/85% $CH_2Cl_2$) to give 3.30 g (64%) of the desired diethyl α-hydroxy PEG-350 mono(methyl ether) phosphonate product as a yellow oil. $^1$H NMR ($CDCl_3$) δ 4.19 (m, 6H), 3.65 (m, 24H), 3.38 (s, 3H), 1.34 (m, 6H) ppm. $^{31}$P NMR ($CDCl_3$) δ 23.1 ppm. IR (neat) 3343, 2872, 1725, 1453, 1248, 1105, 965, 850, 791 $cm^{-1}$.

Synthesis of α-Hydroxy PEG-350 Mono(Methyl Ether) Phosphonic Acid

To a solution containing diethyl α-hydroxy PEG-350 mono(methyl ether) phosphonate (3.61 g, 7.43 mmol) dissolved in methylene chloride (74 mL) was added trimethylsilyl bromide (3.41 g, 22.3 mmol) and the resulting solution was stirred at rt for 2 h. The solvent was removed in vacuo to leave a brown oil. The resulting oil was dissolved in acetone (74 mL) and water (0.5 mL) and the resulting solution was stirred at rt for 1.5 h. The solvent was then removed in vacuo to leave the desired α-hydroxy PEG-350 mono(methyl ether) phosphonic acid product (2.66 g, 84%) as a golden oil. $^1$H NMR ($CDCl_3$) δ 3.65 (m, 24H), 3.38 (s, 3H). $^{31}$P NMR ($CDCl_3$) δ 24.0 ppm. IR (neat) 3460, 2870, 1727, 1456, 1351, 945, 849 $cm^{-1}$.

Example 2

Synthesis of a PEG-1900 Conjugate

Synthesis of PEG-1900 Mono(Methyl Ether) Acetaldehyde

To a solution containing PEG-1900 mono(methyl ether) (16.32 g, 8.60 mmol) dissolved in $CH_2Cl_2$ (86 mL) was added Dess-Martin Periodinane (4.00 g, 9.44 mmol) and the resulting solution was stirred at rt for 20 h. During the reaction a fine, white precipitate was formed and was removed at the end of the reaction via filtration through a celite pad. The solvent was removed from the filtrate in vacuo to leave a white solid which was recrystallized from THF/hexanes to give the desired product (11.6 g, 71%) as a white solid. $^1$H NMR ($CDCl_3$) δ 9.74 (t, J=1 Hz, 1H), 4.17 (d, J=1 Hz 2H), 3.83 (m, 2H), 3.65 (m, 170H), 3.39 (s, 3H).

Synthesis of Diethyl α-Hydroxy PEG-1900 Mono(Methyl Ether) Phosphonate

To a solution containing PEG-1900 mono(methyl ether) acetaldehyde (10.74 g, 5.66 mmol) dissolved in tetrahydrofuran (57 mL) was added diethyl phosphite (0.938 g, 6.79 mmol) followed by 1,8-diazabicyclo[5.4.0]undec-7-ene (1.03 g, 6.79 mmol). The reaction was stirred at rt for 72 h. The solvent was removed in vacuo to leave an orange yellow solid which was recrystallized from THF/hexanes to give the desired product (11.08 g, 96%) as an off white solid. $^1$H NMR ($CDCl_3$) δ 4.18 (m, 4H), 3.64 (m, 172H), 3.38 (s, 3H).

Synthesis of α-Hydroxy PEG-350 Mono(Methyl Ether) Phosphonic Acid

To a solution containing diethyl α-hydroxy PEG-1900 mono(methyl ether) phosphonate (11.08 g, 5.44 mmol) dissolved in methylene chloride (54 mL) was added trimethylsilyl bromide (2.49 g, 16.3 mmol) and the resulting solution was stirred at rt for 3 h. The solvent was removed in vacuo to leave a brown oil. The resulting oil was dissolved in acetone (54 mL) and water (0.5 mL) and the resulting solution was stirred at rt for 16 h. The solvent was then removed in vacuo to leave an orange solid, which was recrystallized from THF/hexanes to give the desired product (10.77 g, 86%) as an off white solid. $^1$H NMR ($CDCl_3$) δ 4.12 (m, 2H), 3.65 (m, 170H), 3.38 (s, 3H).

Comparative Example 3

Synthesis of a Hydrophilic Phosphate

Synthesis of Diphenyl PEG-350 Mono(Methyl Ether) Phosphate

To a solution containing PEG-350 mono(methyl ether) (8.54 g, 24.4 mmol) dissolved in $CH_2Cl_2$ (80 mL) was added triethyl amine (3.68 g, 36.6 mmol) followed by 4-N,N-dimethylaminopyridine (0.298 g, 2.44 mmol). The resulting solution was cooled to 0° C. and diphenyl chlorophosphate (7.87 g, 29.3 mmol) was added dropwise and the reaction was stirred at 0° C. for 10 min. The reaction was then warmed to rt and stirred for an additional 16 h. The reaction was quenched with the addition of 10% HCl (80 mL) and the resulting layers were separated. The organic layer was washed with water (80 mL) and brine (80 mL) and was dried over anhydrous MgSO$_4$. Filtration and removal of the solvent in vacuo left the desired product (14.2 g, 100%) as a golden oil. $^1$H NMR (CDCl$_3$) δ 7.34 (m, 4H), 7.22 (m, 6H), 4.38 (m, 2H), 3.73 (m, 2H), 3.64 (m, 24H), 3.54 (m, 2H), 3.38 (s, 3H).

Synthesis of PEG-350 Mono(Methyl Ether) Phosphoric Acid

To a solution containing diphenyl PEG-350 mono(methyl ether) phosphate (14.2 g, 24.4 mmol) dissolved in acetic acid (108 mL) was added platinum (IV) oxide hydrate (200 mg) and the resulting suspension was heated to 50° C. and placed under an atmosphere of H$_2$ until hydrogen uptake ceased. The reaction was filtered through a celite pad to remove catalyst and the solvent was removed in vacuo to leave the desired product (10.49 g, 100%) as a clear, yellow oil. $^1$H NMR (CDCl$_3$) δ 4.20 (m, 2H), 3.67 (m, 24H), 3.56 (m, 2H), 3.39 (s, 3H).

Example 3

Synthesis of Superparamagnetic Iron Oxide (SPIO) Nanoparticles

A 100 mL three-necked round bottom flask was charged with Fe(acac)$_3$ (0.706 g, 2.0 mmol) and anhydrous benzyl alcohol (20 mL). The resulting solution was sparged with nitrogen and heated to 165° C. for 4 hours under a nitrogen atmosphere. The resulting colloidal suspension of 5 nm iron oxide particles (As determined by DLS) was then cooled to, and stored, at room temperature.

Example 4

Synthesis of α-Hydroxy PEG-350 Mono(Methyl Ether) Phosphonate Coated Superparamagnetic Iron Oxide Nanoparticles To a colloidal suspension of superparamagnetic iron oxide nanoparticles of Example 3 in THF at 1 mg Fe/mL was added the α-hydroxy phosphonic acid conjugate of Example 1 (At a ratio of 1 mol of conjugate per mol of Fe) and the resulting suspension was heated at 50° C. for 16 h. The reaction was then cooled to rt, diluted with water, and the brown aqueous solution was washed three times with hexanes. Any remaining volatiles in the aqueous layer were removed in vacuo and the resulting nanoparticles were purified by washing with H$_2$O against a 30 kDa molecular cutoff filter using tangential flow filtration.

Example 5

Synthesis of α-Hydroxy PEG-1900 Mono(Methyl Ether) Phosphonate Coated Superparamagnetic Iron Oxide Nanoparticles Example 4 was repeated using the conjugate of Example 2 in place of the conjugate of Example 1.

Comparative Example 2

Synthesis of α-Hydroxy PEG-350 Mono(Methyl Ether) Phosphate Coated Superparamagnetic Iron Oxide Nanoparticles Example 4 was repeated using the conjugate of Comparative Example 1.

Example 6

Synthesis of 5-Bromo 1-Pentanal

Oxalyl chloride (2.42 mL, 0.022 mol) was mixed with anhydrous dichloromethane (40 mL) in a 250 mL round bottom flask. The flask was blanketed with nitrogen and the solution was cooled to −78° C. in a dry ice/acetone bath. The reaction mixture was stirred and anhydrous dimethylsulfoxide (3.4 mL, 0.044 mol) was slowly added to the flask followed by 5-bromo-1-pentanol (3.34 g, 0.020 mol) and the reaction mixture was stirred for 15 minutes at −78° C. Triethylamine (14.0 mL, 0.1 mol) was slowly added to the reaction mixture. When the addition of triethylamine was complete, the reaction was stirred for 5 minutes at −78° C. The reaction was removed from the dry ice acetone bath, warmed to room temperature, and stirred for 18 hours at room temperature.

Water (100 mL) was added to the reaction mixture. The two-phase mixture was shaken vigorously in a 500 mL separatory funnel. The aqueous layer was removed and extracted with dichloromethane (100 mL). This dichloromethane was combined with the dichloromethane from the reaction mixture. The combined dichloromethane solution was successively washed with 100 mL each of 1% HCl$_{(aq)}$, water, saturated NaHCO$_{3(aq)}$ and saturated NaCl$_{(aq)}$. The dichloromethane solution was dried with magnesium sulfate and the dichlormethane solution was recovered by filtration. Solvent was removed under vacuum leaving a yellow liquid (1.80 g). The major product was confirmed to be 5-bromo 1-pentanal by $^1$H NMR. $^1$H NMR (400 MHz, CDCl3) δ 9.81 (m, 1H), 3.43 (m, 3H), 2.50 (m, 2H), 2.0-1.4 (m, 8H). The reaction product was carried on to Example 7 without further purification.

Example 7

Synthesis of diethyl (5-bromo-1-hydroxy-pentyl)phosphonate 5-bromopentanal (1.64 g, 0.010 mol) was dissolved in diethylether (15 mL) in a 250 mL round bottom flask. The reaction was blanketed with nitrogen. Lithium perchlorate (7.92 g, 0.075 mol) was added to the reaction and the reaction solution was cooled to 0° C. in an ice bath. Chlorotrimethylsilane (0.631 mL, 0.010 moles) was added to the flask followed by trimethylphosphite (2.1 mL, 0.012 mol). The reaction mixture was stirred for 18 hours at room temperature.

After 18 hours at room temperature water (40 mL) was added to the reaction followed by dichloromethane (40 mL). The organic phase was transferred to a separatory funnel and washed successively with water (40 mL) and brine (40 mL). The methylene chloride solution was dried with magnesium sulfate and filtered to recover the methylene chloride solution. Solvent was removed under vacuum leaving a yellow oil (3.01 g). The oil was characterized by $^1$H NMR and $^{31}$P NMR and the major product was confirmed to be diethyl (5-bromo-1-hydroxy-pentyl)phosphonate. $^1$H NMR (400 MHz, CDCl3) δ 4.25-4.00 (m, 4H), 3.00-3.43 (m, 2H), 1.78-1.95 (m, 2H), 1.78-1.61 (m, 3H), 1.61-1.41 (m, 2H), 1.40-1.25 (m, 6H). $^{31}$P NMR (600 MHz, CDCl3) δ 26.5 (s, 1P), 24.2-24.7 (m, 0.3P). The reaction product was carried on to Example 8 without further purification.

Example 8

Synthesis of diethyl 5-(4-(ethoxycarbonyl)piperidin-1-yl)-1-hydroxypentylphosphonate Diethyl (5-bromo-1-hydroxy-pentyl)phosphonate (3.02 g, 0.0099 mol) was dissolved in anhydrous toluene (100 mL) in a 300 mL round bottom flask. Triethylamine (2.08 mL, 0.015 mol) was added to the reaction mixture followed by ethylisonipecotate (1.84 mL, 0.012 mol). The mixture was heated to reflux for 18 hours. Solvent was removed under vacuum leaving an orange gum. The gum was dissolved in dichloromethane (100 mL) and washed successively with saturated aqueous NaHCO3 (100 mL) and brine (100 mL). The methylene chloride solution was dried with magnesium sulfate and recovered by filtration. Solvent was removed under vacuum leaving an orange liquid (1.70 g).

The orange liquid was purified by silica gel column chromatography. A silica gel column (40 g) was eluted with a solvent gradient starting with 100% dichloromethane and changing to 20% methanol by volume in dichloromethane over 30 minutes. Fractions that contained the product were combined and solvent was removed under vacuum leaving a yellow liquid (0.66 g). The yellow liquid was characterized by $^1$H NMR and the major product was identified as diethyl 5-(4-(ethoxycarbonyl) piperidin-1-yl)-1-hydroxypentyl-phosphonate. $^1$H NMR (400 mHz, CDCl3) δ 4.9-4.5 (s, 1H), 4.2-4 (m, 5H), 3.8-3.7 (m, 1H), 2.9-2.7 (m, 2H), 2.4-2.1 (m, 3H), 2.1-1.9 (m, 2H), 1.9-1.8 (m, 2H), 1.8-1.3 (m, 8H), 1.3-1.2 (m, 5H), 1.2-1.1 (m, 3H). The reaction product was carried to Example 9 without further purification.

Example 9

Synthesis of 5-(4-(ethoxycarbonyl)piperidin-1-yl)-1-hydroxypentylphosphonic acid Diethyl 5-(4-(ethoxycarbonyl)piperidin-1-yl)-1-hydroxy-pentylphosphonate (0.66 g, 0.0017 mol) was dissolved in dichloromethane (25 mL) in a 100 mL flask. Bromotrimethylsilane (0.69 mL, 0.0052 mol) was added to the reaction mixture. The reaction was stirred overnight at room temperature. After overnight stirring, solvent was removed under vacuum leaving an orange gum. The gum was dissolved in acetone (20 mL). Water (0.4 mL) was added. A gum precipitated. Solvent was removed under vacuum leaving a red gum (0.6 g). The gum was characterized by $^1$H NMR and the product determined to be 5-(4-(ethoxycarbonyl)piperidin-1-yl)-1-hydroxypentylphosphonic acid. 1H NMR (400 MHz, CD3OD) δ 4.3-4.1 (m, 2H), 3.9-3.4 (m, 3H), 3.4-2.5 (m, 7H), 2.5-1.35, (m, 11H), 1.35-1.2 (m, 3H).

Example 10

Synthesis of-(4-(ethoxycarbonyl)piperidin-1-yl)-1-Hydroxypentylphosphonate Coated Tantalum Oxide Nanoparticles A solution of anhydrous methanol (17 mL) containing isobutyric acid (0.242 g, 2.75 mmol) and water (0.08 g, 4.44 mmol) was degassed for 40 minutes by sparging with $N_2$. This was added with $Ta_2$ (OEt)$_5$ (1 g, 2.46 mmol) dropwise and the reaction mixture was stirred under $N_2$ atmosphere for 5 h to yield a suspension of 3 to 4 nm nanoparticles. A solution of 5-(4-(ethoxycarbonyl)piperidin-1-yl)-1-hydroxypentylphosphonic acid (0.088 g, 0.205 mmol) in methanol (0.5 mL) was added dropwise to the tantalum oxide nanoparticle suspension (1 mL) and was heated at 70° C. overnight under $N_2$. After cooling to room temperature, water (~3 mL) was added dropwise to the reaction mixture After removing methanol by evaporation at reduced pressure on a rotary evaporator, 1 M NH$_4$OH (0.33 mL) was added and the reaction was stirred at 50° C. overnight. The reaction mixture was dialyzed against DI water (3×2 L) for 24 h using a 3500 Da molecular weight cut-off regenerated celluose membrane. Size was determined to be 7 nm in water by DLS.

Example 11

Characterization of Colloidal Suspensions of SPIO Nanoparticles

The colloidal suspensions obtained as the result of the tangential flow filtration in Examples 4 and 5 and Comparative Example 2 were evaluated for stability and zeta potential.

The hydrodynamic diameter ($D_H$) was measured via dynamic light (DLS) scattering using 150 mM NaCl in water as the suspension medium. The purified SPIO suspension from the tangential flow filtration was diluted into 150 mM NaCl in water and passed through a 100 nm filter to remove dust prior to DLS analysis using a Brookhaven ZetaPALS. The dilution was carried out to yield a minimum of 20,000 counts per second during the DLS measurement. The measurements were made both shortly after the modified nanoparticles were made and after two weeks storage at room temperature. A significant increase in the $D_H$ after storage was an indication that nanoparticles had aggregated and that therefore the particular colloidal suspension was not stable.

The Zeta potential was measured using a Brookhaven ZetaPALS after diluting the purified SPIO suspension from the tangential flow filtration 14× with 10 mM NaCl and passing the diluted SPIO solution through a 100 nm filter to remove dust. The zeta potential for all three colloidal suspensions was within the range±15 mV range commonly accepted as neutral.

The results are set forth in Table 1

TABLE 1

| Nanoparticle Coating | $D_H$ post synthesis | $D_H$ 2 weeks post synthesis | Zeta Potential |
|---|---|---|---|
| PEG-350 α-hydroxy phosphonate | 10 ± 1 nm | 9 ± 1 nm | −0.5 mV |
| PEG-350 Phosphate | 50 ± 1 nm | >100 nm | 7.3 mV |
| PEG-1900 α-hydroxy phosphonate | 20 ± 1 nm | 22 ± 1 nm | −5.0 mV |
| 5-(4-(ethoxycarbonyl)piperidin-1-yl)-1-hydroxypentylphosphonate | 7 ± 1 nm | | −1.7 mV |

Example 12

Imaging of In Vivo Tumors by MRI

All procedures involving animals were completed under protocols approved by the GE Global Research Institutional Animal Care and Use Committee. Tumors were induced in female Fischer 344 rats (~150 g) by subcutaneous injection of 2×10⁶ Mat B III cells (ATCC# CRL1666, ATCC, Manassas, Va.) in 0.1 mL Hank's balanced saline solution. The injection site was located dorsally between the shoulder blades. The tumors were imaged 9 days after implantation, when the tumors were ~1 cm in diameter.

Imaging was conducted on a clinical 3 T GE MR750 scanner using a custom-built, ~6 cm solenoid receive RF coil. To prepare for imaging, the rats were anesthetized by IP injection of ketamine and diazepam using 75 and 5 mg/kg doses, respectively. Once immobile, a 24 gauge catheter was placed in a lateral tail vein and connected to a saline-primed, microbore catheter line extension and stop cock. The dead volume of the catheter, line and stop cock was ~0.5 mL. The prepared animal was then placed within the RF coil and positioned within the bore of the scanner. A pre-injection image set was acquired, and then, without moving the table or the animal, the PEG-350α-hydroxy phosphonate coated superparamagnetic iron oxide nanoparticles were injected via the stop cock followed by a saline flush (~0.8 mL). Immediately following injection (starting 30 s post-injection), image sets were collected throughout a dynamic acquisition period of ~30 minutes resulting in collection of ~16 post-contrast time points. For the injection, SPIO agent was in physiologic saline at a concentration of 10 mg Fe/mL, and was sterile filtered prior to injection and tested for the presence of endotoxin. The agent was dosed at 3 mg Fe/kg body weight.

A 3D fast gradient echo pulse sequence was employed that allowed collection of images at 10 echo times. The imaging slab was positioned via the graphical prescription interface such that the tumor was centered within the transaxial slices and the coverage included the majority of the tumor in depth. The pulse sequence parameters were as follows: pulse sequence: 3D ME fGRE; TE: ranged from 4.1 to 68 ms, with 7.1 ms spacing; TR: 75.5 ms; flip angle: 25 degrees; bandwidth: 62.5 MHz; matrix: 256×256; slice thickness: 0.9 mm; field of view: 8 cm, yielding a voxel size of 0.31×0.31×0.9. The sequence acquisition time was ~2 min.

The imaging data sets were analyzed using a custom software tool (CineTool v8.0.2, GE Healthcare) built upon the IDL platform (IDL v. 6.3, ITT Corp., Boulder, Colo.). In brief, the image analysis tool allowed manual drawing of 3D regions of in interest (ROIs) on the pre-injection series with subsequent calculation of the $T_2^*$ time constant by exponential regression for every voxel within the drawn ROIs at all time points. Representative images and difference maps are given in FIG. 5.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A diagnostic agent composition suitable for injection into a mammalian subject, comprising:
 iron oxide nanoparticles to which are adhered alpha-hydroxy phosphonate moieties, wherein said alpha-hydroxy phosphonate moieties have the formula:

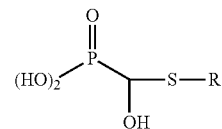

wherein S is a spacer and R is a poly(ethylene oxide) moiety; and
 a pharmaceutically acceptable carrier or excipient.

2. The diagnostic agent composition of claim 1, wherein S is a direct bond, an unsubstituted or a substituted aliphatic or cycloaliphatic group, an unsubstituted or a substituted aryl group, a heteroaliphatic group, a heteroaryl group, or combinations thereof.

3. The diagnostic agent composition of claim 1, wherein S is a straight chain alkyl group of 1 to 10 carbon, atoms in length and n is equal to 1.

4. The diagnostic agent composition of claim 1, wherein the poly(ethylene oxide) moiety comprise a methoxy terminal group.

5. The diagnostic agent composition of claim 1, wherein the poly(ethylene oxide) moiety has a molecular weight less than or equal to about 5000 daltons.

6. The diagnostic agent composition of claim 1, wherein the poly(ethylene oxide) moiety has a molecular weight less than or equal to about 2000 daltons.

7. The diagnostic agent composition of claim 1, wherein the poly(ethylene oxide) moiety has a molecular weight less than or equal to about 350 daltons.

8. The diagnostic agent composition of claim 1, wherein the nanoparticles have an average hydrodynamic particle size ($D_H$) in 150 mM NaCl water as determined by dynamic light scattering of up to about 500 nm.

9. The diagnostic agent composition, of claim 1, wherein the nanoparticles have an average hydrodynamic particle size ($D_H$) in 150 mM NaCl water as determined by dynamic light scattering of up to about 8 nm.

10. The diagnostic agent composition of claim 1, wherein the nanoparticles have a zeta potential between about −15 mV and +15 mV.

11. The diagnostic agent composition of claim 1, wherein the carrier is an isotonic aqueous medium.

12. The diagnostic agent composition of claim 1, in which said nanoparticles are sufficiently hydrophilic to form a stable aqueous colloidal suspension that exhibits no substantial change in hydrodynamic diameter ($D_H$) as determined by dynamic light scattering in 150 mM NaCl water after tangential flow filtration and storage for one week at room temperature.

13. A process for diagnostic imaging comprising:
 a. administering a contrast agent to a subject; and
 b. subjecting said subject to the diagnostic imaging, wherein the contrast agent comprises:
  iron oxide nanoparticles to which are adhered alpha-hydroxy phosphonate moieties, wherein said alpha-hydroxy phosphonate moieties have the formula:

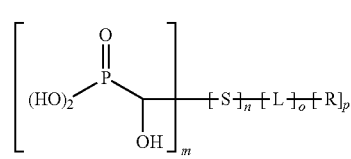

wherein S is a spacer, L is a linkage between S and R, and R is a poly(ethylene oxide) moiety, and wherein m is equal to 1, p is equal to 1-5, and n and o are independently equal to 0-5.

14. The process of claim 13, wherein the contrast agent is administered by injection, inhalation or ingestion.

15. The process of claim 13, wherein the diagnostic imaging is by magnetic resonance (MR).

* * * * *